(12) United States Patent
Abdelatti

(10) Patent No.: US 6,422,873 B1
(45) Date of Patent: Jul. 23, 2002

(54) DEVICE FOR USE IN THE APPLICATION OF CRICOID PRESSURE (FORCE) AND/OR IN TRAINING FOR SUCH APPLICATION

(76) Inventor: Mohamed Osman Abdelatti, Copeland Offices, Birch Hill Hospital, Rochdale OL12 9QB, Lancashire (GB)

( * ) Notice: Subject to any disclaimer, the term of this patent is extended or adjusted under 35 U.S.C. 154(b) by 0 days.

(21) Appl. No.: 09/524,343

(22) Filed: Mar. 13, 2000

(30) Foreign Application Priority Data

Apr. 8, 1999 (GB) .............................................. 9907877
Feb. 14, 2000 (GB) .............................................. 0003128

(51) Int. Cl.<sup>7</sup> .............................................. G09B 23/28
(52) U.S. Cl. ........................ 434/262; 434/265; 600/587; 606/202
(58) Field of Search ................................ 434/262, 265; 600/587; 606/201, 202, 204

(56) References Cited

U.S. PATENT DOCUMENTS 3,276,147 A * 10/1966 Padellford ................... 434/265
5,483,974 A * 1/1996 Crangle ....................... 600/587
5,755,577 A * 5/1998 Gillio .......................... 434/262

FOREIGN PATENT DOCUMENTS

| EP | 0 489 516 A1 | 11/1991 |
| GB | PCT/GB97/03403 | 6/1998 |
| SU | 912162 | 3/1982 |

* cited by examiner

Primary Examiner—Kien T. Nguyen
(74) Attorney, Agent, or Firm—Kohn & Associates

(57) ABSTRACT

A device for use in the correct application and monitoring of the technique of ACF (Applied Cricoid Force) during tracheal intubation comprises a cylinder (1), a piston (2), seal (10) and either an aneroid gauge (3) or a calibrated spring (6) which provides resistance to force applied to the device and at the same time permits monitoring of the force applied. The device may also or alternatively be used as a training tool on a suitable patient substitute e.g. a table, bench or a manikin, until the trainee gains the experience and skills which enable them to reproduce the correct force when applying cricoid force directly on patients.

15 Claims, 2 Drawing Sheets

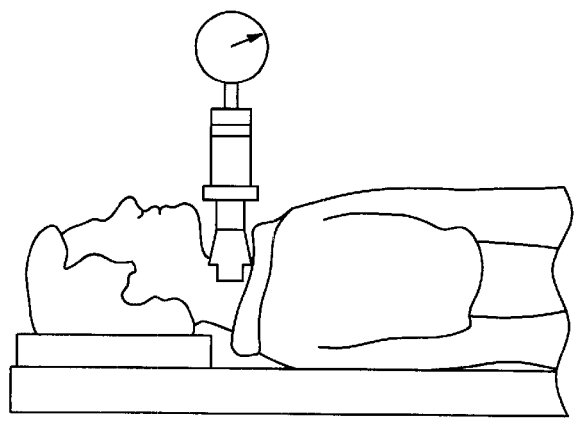
*Figure 1*
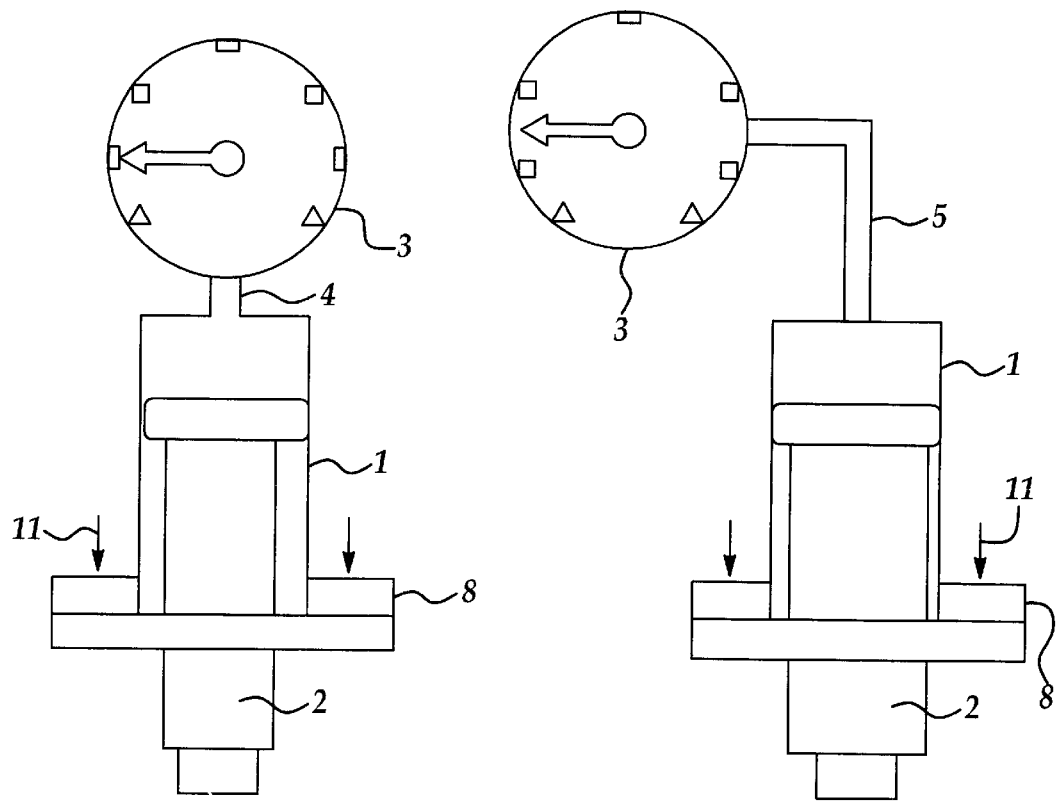
*Figure 2*          *Figure 3*

DEVICE FOR USE IN THE APPLICATION OF CRICOID PRESSURE (FORCE) AND/OR IN TRAINING FOR SUCH APPLICATION

CROSS REFERENCE TO RELATED APPLICATIONS

This application is a United States National Phase application which claims priority on British Application No. GB 99 07877.6, filed Apr. 8, 1999 and British Application No. GB 00 03128.6, filed Feb. 14, 2000.

BACKGROUND OF THE INVENTION

1. Technical Field

This invention relates to a device for training an operative, for example medical personnel and anaesthetic assistants, in the correct application and monitoring of force to the cricoid cartilage of a patient undergoing tracheal intubation, for example at the onset of anaesthesia. It can also be used as device for use directly on patients to apply said force.

2. Background Art

The application of cricoid force is an important technique, which is routinely used during emergency and obstetric anaesthesia. The technique involves the application of external force on the cricoid cartilage (at the front of the neck) to occlude the lumen of the oesophagus which lies behind it. The aim of the technique is to prevent the inhalation of regurgitated stomach contents into the lungs when the patient loses consciousness at the onset of anaesthesia. The inhalation of vomit should it occur is very serious as it causes severe inflammation of the lungs and the outcome may be fatal. Although the technique will be referred to hereinafter with reference to force (as in "applied cricoid force" or ACF) it should be appreciated that the technique is also commonly referred to with reference to pressure (as in "applied cricoid pressure" or ACP). Thus, "force" as used herein is to be interpreted as encompassing "pressure" and vice versa except where such an interpretation would be contrary to the contextual meaning.

Sellick first described the ACF technique, in 1961. It involves the use of three fingers; the index finger is used to apply pressure on the cricoid cartilage and the middle finger and the thumb to stabilise the larynx during the procedure. The force required is equal to 40 Newtons. The anaesthetist's assistant during induction of anaesthesia should consistently maintain this force until the anaesthetist secures the patient airway by inserting a cuffed tracheal tube in the trachea (windpipe).

It is important that the exact force should be applied as the application of an excessive force on the cricoid cartilage distorts the larynx and makes tracheal intubation difficult. On the other hand, if the force is applied is inadequate, the patient may be subjected to the dangers of inhalation of stomach contents.

Several studies have shown that it is difficult to consistently apply the exact cricoid force and that there is wide individual variation in the ACF with 47%–61% of medical staff applying an inadequate force. It has also been shown that to apply the correct force, frequent training in the manoeuvre is required as retention of skills after acquiring the experience is short lived To gain experience, trainees practice on weight scales to be able to manually reproduce the correct ACF. It is also possible to train anaesthetic assistants to reproduce the correct force during simulated ACF but mechanical simulators are not readily available and are expensive. It is, therefore, necessary to provide a simple and readily available training tool to allow frequent training and to maintain skills. No training devices currently exist but a few devices for the application of the ACF directly on a patient are available. However, they have not been widely adopted in clinical practice. This is largely because of various shortcomings including complexity, expense, reliance on electricity/battery supply, delay in setting up the equipment when urgently required or they are heavy resulting in laryngeal distortion and difficult tracheal intubation. For these reasons, currently, manual application of cricoid pressure, with its aforesaid shortcomings, remains the predominant method.

It is one aim of the present invention to provide means for enabling ACF to be applied correctly, and consistently, for a sufficient period of time. It is a further aim of the present invention to provide means for training an operative in the ACF procedure.

It is yet a further aim of the present invention to provide means for both the application of cricoid force to a patient, and for training an operative to do so.

It is yet a further aim of the present invention to provide an ACF device and/or training device which addresses the problems of prior art devices of this type, whether referred to herein or otherwise.

SUMMARY OF THE INVENTION

According to a first aspect of the present invention there is provided a device for use in the application of force to the cricoid cartilage of a patient undergoing tracheal intubation, the device including means for transmitting force applied to the device to the cricoid cartilage and means for monitoring the force applied.

According to a second aspect of the present invention there is provided a device for use in training an operative in the reproduction of a desired force intended to be applied by the person so trained to the cricoid cartilage of a patient undergoing tracheal intubation, the device including means for transmitting force applied to the device to a patient substitute and means for monitoring the force applied.

According to a third aspect of the present invention there is provided a kit of parts for use in both the training of an operative in the application of force to the cricoid cartilage of a patient undergoing tracheal intubation and in the actual application of said force to such a patient, is the kit comprising a device having means for transmitting force applied to the device to a patient or a patient substitute and means for monitoring the force applied, together with an intermediate component for connecting between the device and the cricoid cartilage of a patient.

Preferably, the device comprises a first part which may be placed directly, or indirectly by means of an intermediate component, on the cricoid cartilage, and a second part coupled to said first part whereby force applied to the second part is transmitted to the first part.

Conveniently, the second part includes a cylinder and the first part includes a piston disposed within the cylinder for movement relative thereto into and out of one end of the cylinder.

Preferably, a seal is provided between the piston and the other end of the cylinder.

Preferably, the means for monitoring the force applied comprises means for monitoring the degree of compression of the space within the cylinder above the piston against a resistive force.

The resistive force may be supplied by a spring disposed between the first part and the second part.

Preferably, the spring is calibrated to indicate the force applied to the device.

Alternatively, the resistive force may be supplied by a pressure gauge in communication with the space within the cylinder above the piston.

For convenience of use, the device preferably includes extension means on which one or more fingers may be placed to apply force manually to the device. For example, the extension means may comprise one or more wings.

The device may be used as it is for the purpose of training an operative in the use of the ACF procedure, by placing the tip (distal end) of the piston on a hard surface or on a manikin, but in order that the same device may be used in the actual application of ACF to a patient, an intermediate component in the form of a U-shaped cricoid yoke is provided between the first part and the patient's cricoid cartilage.

This yoke, which is preferably moulded from rubber or foam, is conveniently fixed onto the distal end of the piston, to convert the device from a training device into a device for using the ACF procedure on a patient.

According to a fourth aspect of the present invention there is provided a method of applying a desired force to the cricoid cartilage of a patient undergoing tracheal intubation, the method including using on said patient a device having means for transmitting force applied to the device to the patient, and monitoring the force applied.

According to a fifth aspect of the present invention there is provided a method of training an operative in the technique of applied cricoid force (ACF), the method comprising applying force to a patient substitute such as is a hard surface or a manikin using a device having means for monitoring the force applied.

BRIEF DESCRIPTION OF THE DRAWINGS

Embodiments of the present invention will now be described by way of example only with reference to the accompanying drawings in which:

FIG. 1 is a schematic diagram to illustrate the ACF manoeuvre using a first embodiment of the invention.

FIG. 2 shows the embodiment of FIG. 1 with an aneroid pressure gauge attached to the nozzle of the syringe cylinder.

FIG. 3 shows a variant of the embodiment of FIG. 1 with the gauge connected to the nozzle of the cylinder via an extension tubing to monitor the ACF at a distance from the patient.

DETAILED DESCRIPTION OF THE PREFERRED EMBODIMENTS

Figure 4:
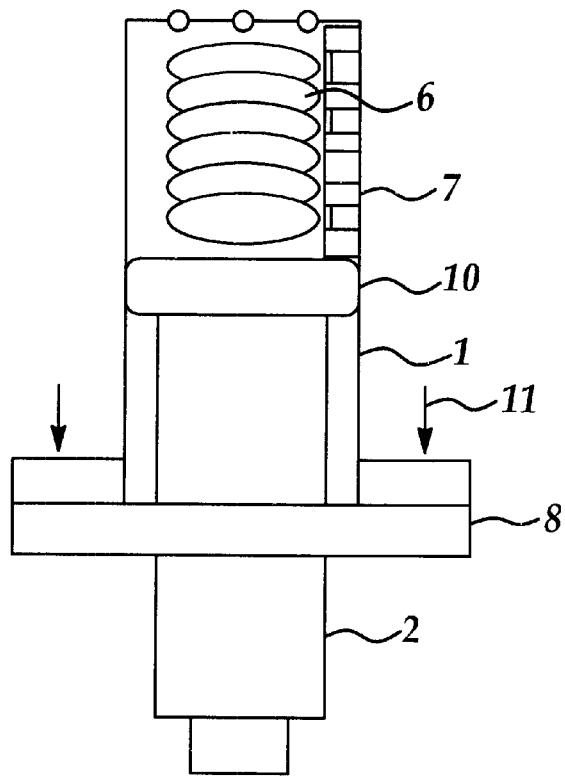
FIG. 4 shows a second embodiment of the invention.

Referring to the drawings, a first embodiment of the invention comprises a plastic cylinder 1, a piston 2 with seal 10 and an aneroid pressure gauge 3 connected to the nozzle of the cylinder 4 either directly as in FIG. 2 or via a plastic tubing 5 as in FIG. 3. The device of FIGS. 1, 2 and 3 can be calibrated to indicate the ACF using any conventional scales weighing up to 10 kg (1 kg=9.81N). The calibration should be done at room temperature and after the device has warmed up in hand to simulate normal operating temperature. To calibrate the device, the piston was drawn to a distance half way inside the cylinder. Force was applied with the thumb on one wing of the cylinder and the index and middle fingers on the second wing and gradually increased until a calibration point is reached (e.g. 20N=2.04 kg). The value of force obtained on the weight scale was matched with that recorded by the gauge. The procedure was repeated to mark the 40N or 4.09 kg and other intermediate points.

A second embodiment of the invention is shown in FIG. 4. It is similar to the first embodiment except that instead of the pressure gauge, a calibrated spring 6, inserted inside the barrel of the cylinder 1 in the space between the seal 10 and the nozzle, is used for monitoring the ACF. Any conventional scale can similarly be used to calibrate this prototype. The values of force obtained on the weight scale are then marked on a self-adhesive label 7 attached along the barrel of the cylinder. The end of the cylinder 1 above the piston has air outlets to allow compression of the spring.

Figure 5:
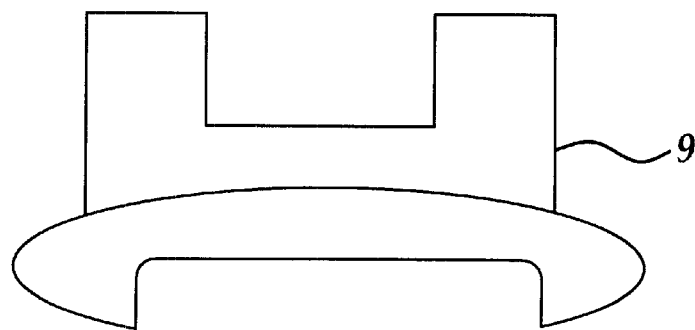
FIG. 5 shows the intermediate component, namely a U-shaped rubber or foam cricoid yoke with a compatible slot to fit the tip of the piston.

FIG. 5 shows the cricoid yoke. Both embodiments can be converted into cricoid devices for direct use on patients by slotting the distal end of the piston of either prototype into this, compatible U-shaped, rubber or foam-moulded cricoid yoke 9. When the devices are not connected to the cricoid yoke they can be used as training tools to allow trainees to practice the correct force e.g. on a bench, a table or a manikin in order to be able subsequently to use the correct force when applying a three-finger technique directly to a patient. The procedure of using the devices as training tools is as follows:

1. Hold the device like a pen with a tip of the piston 2 pointing downward.
2. Place the tip of the piston on a hard surface (e.g. bench or table).
3. Place the tips of the index and middle fingers on one wing 8 of the cylinder and that of the thumb on the second wing 8.
4. Apply pressure on the wings of the cylinder.
5. Read the Applied pressure/force off the attached scale/gauge 7/3.
6. Continue training until it is possible to reproduce the correct force.

After attaching the compatible yoke to the tip of the piston the devices can be used directly on patients as follows:

First, palpate the front of the neck to localise the cricoid cartilage. Then, place the U-shaped rubber yoke 9 over it. To apply the desired pressure or force on the cricoid cartilage, hold the device like a pen and place the thumb on one of the wings 8 on the cylinder and the index and middle fingers on the second wing 8. Then press downwards (see the direction of the arrows 11 and read the cricoid pressure/force off the gauge 3 or the scale 7. This applied force or pressure should be maintained until the trachea is intubated.

Any feature of any aspect of any invention or embodiment described herein may be combined with any feature of any aspect of any other invention or embodiment described herein.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

What is claimed is:

1. A device for use in training an operative in the reproduction of a desired force intended to be applied by the person so trained to the cricoid cartilage of a patient undergoing tracheal intubation, the device including means for transmitting force applied to the device to a patient substitute; means for monitoring the force applied; and extension means comprising one or more wings on which one or more fingers can be placed to apply force manually to the device.

2. A device according to claim 1 and including a first part which can be placed directly, or indirectly by means of an intermediate component, on the cricoid cartilage, and a second part coupled to said first part whereby force applied to the second part is transmitted to the first part.

3. A device according to claim 2 wherein the second part includes a cylinder and the first part includes a piston disposed within the cylinder for movement relative thereto into and out of one end of the cylinder.

4. A device according to claim 3 wherein a seal is provided between the piston and the other end of the cylinder.

5. A device according to claim 3 wherein the means for monitoring the force applied comprises means for monitoring the degree of compression of the space within the cylinder above the piston against a resistive force.

6. A device according to claim 5 wherein the resistive force is supplied by a spring disposed between the piston and the other end of the cylinder.

7. A device according to claim 6 wherein the spring is calibrated to indicate the force applied to the device.

8. A device according to claim 5 wherein the resistive force is supplied by a pressure gauge in communication with the space within the cylinder above the piston.

9. A device according to claim 2 wherein an intermediate component in the form of a U-shaped cricoid yoke is provided between the first part and the patient's cricoid cartilage.

10. A device according to claim 9 wherein the yoke is moulded from rubber or foam.

11. A device according to claim 2 the second part is made from plastics material.

12. A device for use in the application of force to the cricoid cartilage of a patient undergoing tracheal intubation, the device including means for transmitting force applied to the device to the cricoid cartilage and means for monitoring the force applied; and extension means comprising one or more wings on which one or more fingers can be placed to apply force manually to the device.

13. A kit of parts for use in both the training of an operative in the application of force to the cricoid cartilage of a patient undergoing tracheal intubation and in the actual application of said force to such a patient, the kit comprising a device having means for transmitting force applied to the device to a patient or a patient substitute; means for monitoring the force applied, together with an intermediate component for connecting between the device and the cricoid cartilage of a patient; and extension means comprising one or more wings on which one or more fingers can be placed to apply force manually to the device.

14. A method of training an operative in the technique of applied cricoid force (ACF), the method comprising applying force to a patient substitute using a device having means for monitoring the force applied and extension means comprising one or more wings, placing one or more fingers on at least one of said wings to apply force manually to said device.

15. A method of applying a desired force to the cricoid cartilage of a patient undergoing tracheal intubation, the method including using on said patient a device having means for transmitting force applied to the device to the patient, and extension means comprising one or more wings on which one or more fingers can be placed to apply force manually to the device; and monitoring the force applied.

* * * * *